US008980557B2

(12) United States Patent
Nishiyama et al.

(10) Patent No.: US 8,980,557 B2
(45) Date of Patent: Mar. 17, 2015

(54) MARKER FOR DETERMINATION OF SENSITIVITY TO TRIPLET COMBINATION ANTI-CANCER AGENT

(75) Inventors: Masahiko Nishiyama, Kokubunji (JP); Hidetaka Eguchi, Iruma (JP); Satoru Wada, Kawagoe (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 13/991,318

(22) PCT Filed: Dec. 2, 2011

(86) PCT No.: PCT/JP2011/077890
§ 371 (c)(1),
(2), (4) Date: Jun. 3, 2013

(87) PCT Pub. No.: WO2012/074085
PCT Pub. Date: Jun. 7, 2012

(65) Prior Publication Data
US 2013/0302327 A1    Nov. 14, 2013

(30) Foreign Application Priority Data

Dec. 3, 2010  (JP) ................................. 2010-270634

(51) Int. Cl.
| C12Q 1/68 | (2006.01) |
| A61K 45/06 | (2006.01) |
| A61K 31/282 | (2006.01) |
| A61K 31/513 | (2006.01) |
| A61K 31/519 | (2006.01) |
| A61K 33/24 | (2006.01) |
| G01N 33/574 | (2006.01) |
| G06F 19/00 | (2011.01) |

(52) U.S. Cl.
CPC ............... *A61K 45/06* (2013.01); *A61K 31/282* (2013.01); *A61K 31/513* (2013.01); *A61K 31/519* (2013.01); *A61K 33/24* (2013.01); *C12Q 1/6886* (2013.01); *G01N 33/57419* (2013.01); *C12Q 2600/106* (2013.01); *C12Q 2600/136* (2013.01); *C12Q 2600/158* (2013.01); *G01N 2800/52* (2013.01); *G06F 19/3481* (2013.01)
USPC .......................................................... 435/6.1

(58) Field of Classification Search
CPC .................... A61K 39/00; C12Q 1/68
See application file for complete search history.

(56) References Cited

U.S. PATENT DOCUMENTS

2012/0129880 A1   5/2012 Nishiyama et al.

FOREIGN PATENT DOCUMENTS

| JP | 2009 050189 | 3/2009 |
| WO | 2010 103851 | 9/2010 |

OTHER PUBLICATIONS

Wetmur et al (PNAS, 1986, 83: 7703-7707).*
Watanabe et al (Cancer, 2009, 115(2): 283-292).*
Tockman et al (Cancer Res., 1992, 52:2711s-2718s).*
English translation of Written Opinion Issued Jan. 24, 2011 in PCT/JP11/077890 filed Dec. 2, 2011.
International Search Report issued Jan. 24, 2012, in PCT/JP11/77890 filed Dec. 2, 2011.
Lee, J. J. et al., "An Update on Treatment Advances for the First-Line Therapy of Metastatic Colorectal Cancer", The Cancer Journal, vol. 13, No. 5, pp. 276-281, (Sep./Oct. 2007).
Chua, W. et al. "Molecular Markers of Response and Toxicity to FOLFOX Chemotherapy in Metastatic Colorectal Cancer", British Journal of Cancer, vol. 101, No. 6, pp. 998-1004, (2009).
Ross, J. S. et al., "Biomarker-Based Prediction of Response to Therapy for Colorectal Cancer", Am. J. Clin. Pathol, vol. 134, No. 3, pp. 478-490, (2010).
Braun, M. S. et al., "Predictive Biomarkers of Chemotherapy Efficacy in Colorectal Cancer: Results From the UK MRC FOCUS Trial" Journal of Clinical Oncology, vol. 26, No. 16, pp. 2690-2698 and 4363, (Jun. 1, 2008).
Chinese Office Action issued Feb. 20, 2014, in China Patent Application No. 201180058258.1 (with English Abstract).
Shu-Qiang Yuan, et al., "Correlation of chemosensitivity measured by histoculture drug response assay to expression of multidrug resistance genes and proteins in gastric cancer", Chinese Journal of Cancer, vol. 28, No. 4, 2009, pp. 337-343.
Extended European Search Report issued Mar. 21, 2014 in Patent Application No. 11846035.1.
S-W Han, et al., "Phase II study and biomarker analysis of cetuximab combined with modified FOLFOX6 in advanced gastric cancer" British Journal of Cancer, vol. 100, No. 2, Jan. 6, 2009, XP055107283, pp. 298-304.

* cited by examiner

*Primary Examiner* — Sean Aeder
(74) *Attorney, Agent, or Firm* — Oblon, McClelland, Maier & Neustadt, L.L.P.

(57) ABSTRACT

To provide a marker for determining sensitivity of a patient to an anti-cancer agent, which marker can determine whether or not the patient has a therapeutic response to the anti-cancer agent, and novel cancer therapeutic means employing the marker.

The marker for determining the sensitivity of a subject to an anti-cancer agent including oxaliplatin or a salt thereof, fluorouracil or a salt thereof, and levofolinate or a salt thereof, the marker containing one or more genes selected from the group consisting of ALAD gene, C20orf43 gene, CABLES1 gene, CDC14B gene, GDA gene, HOXB6 gene, RPL7AP27 gene, TMEM18 gene, and UGT2B10 gene.

8 Claims, 1 Drawing Sheet

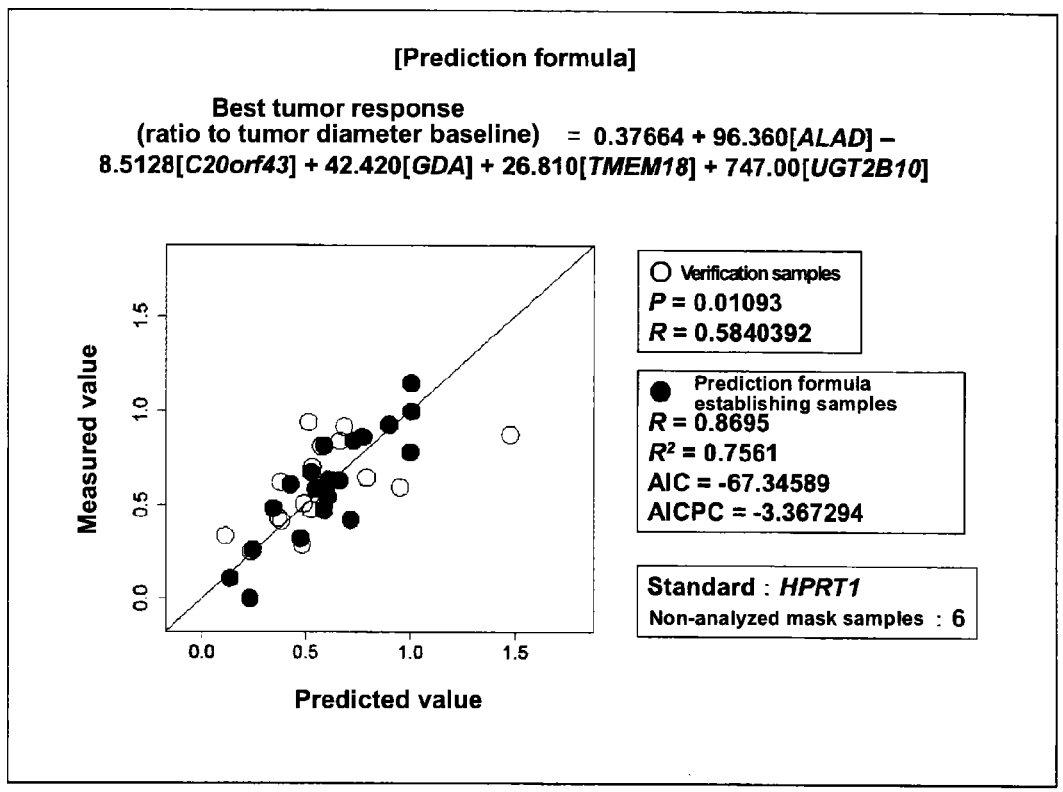

MARKER FOR DETERMINATION OF SENSITIVITY TO TRIPLET COMBINATION ANTI-CANCER AGENT

CROSS REFERENCE TO RELATED APPLICATIONS

The present application is a 35 U.S.C. §371 national stage patent application of international patent application PCT/JP2011/077890, filed on Dec. 2, 2011, published as WO 2012/074085 on Jun. 7, 2012, the text of which is incorporated by reference, and claims the benefit of the filing date of Japanese Application No. 2010-270634, filed on Dec. 3, 2010, the text of which is also incorporated by reference.

TECHNICAL FIELD

The present invention relates to a marker for use in determination of the sensitivity of a cancer patient to an anti-cancer agent to be administered thereto, which marker can determine whether or not the cancer of the patient has a therapeutic response to the anti-cancer agent, and to application of the marker.

BACKGROUND ART

Anti-cancer agents have various types such as an alkylating agent, a platinum agent, an antimetabolite, an antitumor antibiotic, and an antitumor plant alkaloid. These anti-cancer agents are effective for some cancers but not effective for other cancers. Even when an anti-cancer agent has been confirmed to be effective for a certain cancer, the anti-cancer agent is effective for some patients and not effective for other patients, leading to interindividual differences. Whether or not a cancer of a specific patient has response to an anti-cancer agent is designated as sensitivity to the anti-cancer agent.

Oxaliplatin (L-OHP) is a platinum-based complex anti-cancer agent. Similar to cisplatin (CDDP) and carboplatin (CBDCA), which are other platinum-based complex anti-cancer agents, the action mechanism thereof is thought to be based on inhibition of DNA synthesis or protein synthesis via cross-linking with DNA bases. L-OHP exhibits anti-tumor effect on colorectal cancer, to which CDDP or CBDCA is ineffective, and shows different spectrum of anti-tumor activity from that of a precedent platinum-based complex anti-cancer agent. In the United States of America, L-OHP for use in combination with fluorouracil (5-FU)/levofolinate (LV) was approved as a first line therapy for metastatic colorectal cancer in January, 2004. In Japan, L-OHP was listed in the National Health Insurance price list in the case of combination use thereof with continuous infusional LV and 5-FU (FOLFOX4 regimen) for "advanced/recurrent colorectal cancer not amenable to curative surgical resection" in April, 2005. Until the early 1990's, 5-FU/LV regimen to advanced/recurrent colorectal cancer has provided a survival of 10 to 12 months. In contrast, a FOLFOX regimen combined with L-OHP results in a prolonged survival of 19.5 months (about twice the survival time). In August, 2009, an indication of L-OHP combined with continuous infusional 5-FU/LV to "postoperative adjuvant chemotherapy for colon cancer" was added to efficacy and effectiveness. Thus, L-OHP is a promising drug having an efficacy in an increased number of colorectal cancer patients.

Meanwhile, 5-FU is a fluoro-pyrimidine anti-cancer agent developed in 1957 and even now serves as a basic drug for use in the chemotherapy of gastrointestinal cancer. When incorporated into cancer cells, 5-FU exerts cytotoxic effect through a principle action mechanism of DNA synthesis inhibition induced by inhibition of thymidylate synthase (TS) by an active metabolite, fluorodeoxyuridine-5'-monophosphate (FdUMP), and another mechanism of RNA function inhibition by another active metabolite, 5-fluorouridine triphosphate (FUTP).

Meanwhile, clinical performance including survival rate attained by chemotherapy of advanced or metastatic colorectal cancer has been drastically improved through a combination therapy employing a key drug such as irinotecan (CPT-11) or L-OHP, which was developed in the 1990s, and a fluoro-pyrimidine drug such as 5-FU, which has been a main drug for the therapy of colorectal cancer. However, the response rate of such chemotherapy is as low as about 50%. That is, the chemotherapy is not effective for half of the patients to whom an anti-cancer agent has been administered with high risks such as serious adverse events. Thus, in order to provide an optimum regimen in cancer chemotherapy, there is urgent demand for establishing a marker for predicting the sensitivity of a patient to an anti-cancer agent, which marker enables determination of therapeutic response of individual patients (i.e., indication of a responder or non-responder).

Generally, the therapy schedule of cancer chemotherapy requires a long period of time. After repetition of several courses of chemotherapy while emergence of adverse events is monitored, attainment of a therapeutic effect and continuation of the therapy are assessed. The assessment requires a long period of time and high medical cost, and the adverse events have actually been observed to a certain degree. Thus, if there were means for predicting whether or not individual patients can receive the effect of chemotherapy before or in an early stage of the therapy, the burden of the patients and emergence of adverse events can be reduced or mitigated, leading to reduction in medical cost.

Large-scale prospective clinical trial (FOCUS trial) for investigating biomarkers that predict therapeutic response of advanced colorectal cancer patients to chemotherapy has revealed that only topoisomerase-1 (Topo1) exhibits weak relationship with the 5-FU/L-OHP combination therapy as an effect predicting factor (Non-Patent Document 1). This indicates that there has been established no technique that can reliably select a patient who is expected to be effectively treated through the 5-FU/L-OHP combination therapy. Therefore, there is keen demand for establishment of a biomarker that can predict the effect of the FOLFOX regimen employing a triplet combination of L-OHP/5-FU/LV or that can diagnose the therapeutic response to the FOLFOX regimen in an early stage.

PRIOR ART DOCUMENTS

Non-Patent Documents

Non-Patent Document 1: J. Clin. Oncol. 26, 2690-2698 (2008)

SUMMARY OF THE INVENTION

Problems to be Solved by the Invention

An object of the present invention is to provide a marker for determining sensitivity of a patient to an anti-cancer agent (hereinafter the marker may be referred to as an "anti-cancer agent sensitivity determination marker"), which marker can determine whether or not the patient has a therapeutic response to the anti-cancer agent. Another object is to provide novel cancer therapeutic means employing the marker.

Means for Solving the Problems

In view of the foregoing, the present inventors have conducted comprehensive analysis of gene expression and therapeutic sensitivity by using cancer tissue samples from cancer patients who received a fluorouracil/levofolinate/oxaliplatin combination therapy, whereby nine genes conceivably involved in the sensitivity have been specified. The inventors have also found that five genes of the nine specified genes are particularly useful. Based on these findings, the inventors have further investigated, and have found that, by determining the gene expression levels of a biological sample derived from a cancer patient, whether or not the cancer of the cancer patient has sensitivity to a specific anti-cancer agent can be determined; that the sensitivity of a patient to an anti-cancer agent, specifically, the best tumor response (ratio), can be calculated by inputting the expression levels of the genes to a specific calculation formula; that, by employing a variation in gene expression as an index, an anti-cancer agent sensitivity-enhancing agent can be selected through screening; and that, by employing the sensitivity-enhancing agent in combination with an anti-cancer agent which is a target of sensitivity enhancement, the therapeutic effects of the anti-cancer agent can be remarkably enhanced. The present invention has been accomplished on the basis of these findings.

Accordingly, the present invention provides a marker for determining the sensitivity of a subject to an anti-cancer agent including oxaliplatin or a salt thereof, fluorouracil or a salt thereof, and levofolinate or a salt thereof, the marker comprising one or more genes selected from the group consisting of ALAD gene, C20orf43 gene, CABLES1 gene, CDC14B gene, GDA gene, HOXB6 gene, RPL7AP27 gene, TMEM18 gene, and UGT2B10 gene.

The present invention also provides a specific embodiment of the determination marker, wherein said one or more genes are ALAD gene, C20orf43 gene, GDA gene, TMEM18 gene, and UGT2B10 gene.

The present invention also provides a specific embodiment of the determination marker, which predicts best tumor response (ratio).

The present invention also provides a method for determining the sensitivity of a subject to an anti-cancer agent including oxaliplatin or a salt thereof, fluorouracil or a salt thereof, and levofolinate or a salt thereof, the method comprising measuring the expression levels of one or more genes selected from the group consisting of ALAD gene, C20orf43 gene, CABLES1 gene, CDC14B gene, GDA gene, HOXB6 gene, RPL7AP27 gene, TMEM18 gene, and UGT2B10 gene in a specimen.

The present invention also provides a specific embodiment of the determination method, the method comprising measuring the expression levels of ALAD gene, C20orf43 gene, GDA gene, TMEM18 gene, and UGT2B10 gene.

The present invention also provides a specific embodiment of the determination method, the method further comprising calculating best tumor response (ratio) by the following formula (1):

Best tumor response(ratio)=$0.37664+96.360 \times A - 8.5128 \times B + 42.420 \times C + 26.810 \times D + 747.00 \times E$ (1)

(wherein A represents an expression level of ALAD gene; B represents an expression level of C20orf43 gene; C represents an expression level of GDA gene; D represents an expression level of TMEM18 gene; and E represents an expression level of UGT2B10 gene).

The present invention also provides a kit for carrying out the determination method, the kit comprising a protocol for measuring the expression levels of one or more genes selected from the group consisting of ALAD gene, C20orf43 gene, CABLES1 gene, CDC14B gene, GDA gene, HOXB6 gene, RPL7AP27 gene, TMEM18 gene, and UGT2B10 gene in a specimen.

The present invention also provides a screening method for a sensitivity-enhancing agent to an anti-cancer agent including oxaliplatin or a salt thereof, fluorouracil or a salt thereof, and levofolinate or a salt thereof, the method comprising employing, as an index, a variation in expression of one or more genes selected from the group consisting of ALAD gene, C20orf43 gene, CABLES1 gene, CDC14B gene, GDA gene, HOXB6 gene, RPL7AP27 gene, TMEM18 gene, and UGT2B10 gene in a specimen.

The present invention also provides a sensitivity-enhancing agent to an anti-cancer agent including oxaliplatin or a salt thereof, fluorouracil or a salt thereof, and levofolinate or a salt thereof, the agent having been obtained through the screening method.

The present invention also provides a composition for cancer therapy comprising the aforementioned sensitivity-enhancing agent, and an anti-cancer agent including oxaliplatin or a salt thereof, fluorouracil or a salt thereof, and levofolinate or a salt thereof.

Effects of the Invention

By use of the anti-cancer agent sensitivity determination marker of the present invention, the anti-cancer agent therapeutic response of a patient can be correctively determined before administration of or in an early stage after administration of the anti-cancer agent. As a result, an anti-cancer agent having higher therapeutic effect can be selected, and progression of cancer and aggravation of adverse effects, which results from continuous administration of an anti-cancer agent exerting no expected therapeutic effect, can be prevented. Thus, reductions can be expected in burden of the patient and medical cost. By use of the determination marker, a drug which enhances the sensitivity to an anti-cancer agent can be selected through screening. By employing the sensitivity-enhancing agent in combination with the anti-cancer agent targeted by the sensitivity-enhancing agent, the cancer therapeutic effect can be remarkably enhanced.

BRIEF DESCRIPTION OF THE DRAWINGS

[FIG. 1] A graph showing a formula for predicting the best tumor response (ratio) under administration of L-OHP/5-FU/LV in triple combination, established from the expression levels of five genes of the invention, and showing the utility of the prediction.

MODES FOR CARRYING OUT THE INVENTION

The anti-cancer agent sensitivity determination marker of the present invention comprises one or more genes selected from the group consisting of ALAD gene, C20orf43 gene, CABLES1 gene, CDC14B gene, GDA gene, HOXB6 gene, RPL7AP27 gene, TMEM18 gene, and UGT2B10 gene. The genes of the present invention are thought to have correlation with anti-cancer agent sensitivity, which has been estimated by correlation analysis of the results obtained by comprehensive analysis of gene expression levels in cancer tissue samples from cancer patients who received a fluorouracil/levofolinate/oxaliplatin combination therapy. Among these genes, five genes; ALAD gene, C20orf43 gene, GDA gene, TMEM18 gene, and UGT2B10 gene, are particularly useful. By use of the five genes, the best tumor response (ratio) of a target cancer patient can be predicted.

In the present invention, ALAD gene refers to a gene expressing mRNA having a nucleotide sequence defined by GenBank Accession No. NM_000031, or a homologue of the gene;

C20orf43 gene refers to a gene expressing mRNA having a nucleotide sequence defined by GenBank Accession No. NM_016407, or a homologue of the gene;

CABLES1 gene refers to a gene expressing mRNA having a nucleotide sequence defined by GenBank Accession No. NM_138375, or a homologue of the gene;

CDC14B gene refers to a gene expressing mRNA having a nucleotide sequence defined by GenBank Accession No. NM_033331, or a homologue of the gene;

GDA gene refers to a gene expressing mRNA having a nucleotide sequence defined by GenBank Accession No. NM_004293, or a homologue of the gene;

HOXB6 gene refers to a gene expressing mRNA having a nucleotide sequence defined by GenBank Accession No. NM_018952, or a homologue of the gene;

RPL7AP27 gene refers to a gene defined by Entrez Gene ID152663, or a homologue of the gene;

TMEM18 gene refers to a gene expressing mRNA having a nucleotide sequence defined by GenBank Accession No. NM_152834, or a homologue of the gene; and UGT2B10 gene refers to a gene expressing mRNA having a nucleotide sequence defined by GenBank Accession No. NM_001075, or a homologue of the gene.

As used herein, the term "gene" refers not only to double strand DNA but also to single strand DNA forming the double strand DNA such as a sense strand or an antisense strand. No particular limitation is imposed on the length of the DNA. Examples of the nucleic acid (polynucleotide) include RNA and DNA. Specific examples of DNA include cDNA, genomic DNA, and synthetic DNA, and specific examples of RNA include mRNA, rRNA, and siRNA. The term "polynucleotide" also encompasses an oligonucleotide consisting of a plurality of nucleotides.

The method of the present invention for determining the sensitivity of a subject to an anti-cancer agent may be carried out by measuring the expression levels of one or more genes selected from the aforementioned nine genes in a specimen. Among the nine genes, five genes; ALAD gene, C20orf43 gene, GDA gene, TMEM18 gene, and UGT2B10 gene, are particularly useful. Thus, by measuring the expression levels of the five genes in the specimen and calculating the best tumor response (ratio) from the expression levels by formula (1), the sensitivity of the target cancer patient to an anti-cancer agent can be determined.

Specifically, a multiple regression analysis was performed between the expression level of each gene in the cancer tissue specimens obtained from cancer patients and the best tumor response (ratio) of the relevant patients (see Shimokuni T et al., "Chemosensitivity prediction in esophageal squamous cell carcinoma: novel marker genes and efficacy-prediction formulae using their expression data." Int. J. Oncol. 2006. 5). The analysis has revealed that the values obtained by inputting the expression levels of the aforementioned five genes (i.e., ALAD gene, C20orf43 gene, GDA gene, TMEM18 gene, and UGT2B10 gene) into the formula (1) have considerably high correlation to the best tumor response (ratio).

Therefore, through measuring the expression levels of the aforementioned five genes in the specimen and inputting the measurements into the following formula (1), the sensitivity of a subject to an anti-cancer agent of interest can be determined, and specifically the best tumor response (ratio) can be predicted.

$$\text{Best tumor response(ratio)} = 0.37664 + 96.360 \times A - 8.5128 \times B + 42.420 \times C + 26.810 \times D + 747.00 \times E \quad (1)$$

(wherein A represents an expression level of ALAD gene; B represents an expression level of C20orf43 gene; C represents an expression level of GDA gene; D represents an expression level of TMEM18 gene; and E represents an expression level of UGT2B10 gene).

For carrying out the method of the present invention for determining the sensitivity of a subject to an anti-cancer agent, the expression levels of the aforementioned nine genes in a specimen may be measured. Examples of the specimen include biological samples derived from a subject having cancer (cancer patient) such as blood, serum, plasma, urine, tumor tissue and cells, ascites, pleural fluid, cerebrospinal fluid, feces, and sputum. Among them, tumor tissue is particularly preferred. The specimen may be treated with an appropriate known method and employed as a tissue extract, a tissue preparation, etc.

Examples of the cancer to which the present invention is applied include lip, oral, and pharyngeal cancers, typically pharyngeal cancer; digestive cancers such as esophageal cancer, gastric cancer, and colorectal cancer; respiratory and intrathoracic organ cancers such as lung cancer; bone and articular cartilage cancers, malignant skin melanoma, squamous cell carcinoma, and other skin cancers; mesothelial and soft tissue cancers such as mesothelioma; female genital cancers such as breast cancer, uterine cancer, and ovarian cancer; male genital cancers such as prostate cancer; urinary tract cancers such as bladder cancer; eye, brain, and central nervous system cancers such as brain tumor; thyroid and other endocrine cancers; lymphoid tissue, hematopoietic tissue, and other related tissue cancers such as non-Hodgkin's lymphoma and lymphoid leukemia; and metastatic cancers from the aforementioned cancers as primary foci. Among them, the present invention is preferably applied to colorectal cancer (colon cancer). Particularly preferably, the present invention is applied to cancer before chemotherapy.

The gene expression level may be measured by use of a probe or primer which can detect the genes of the present invention or mRNA thereof, whereby the copy number or expression level of a target gene is determined through the northern hybridization method, the DNA microarray method, the real-time PCR method, the RT-PCR method, or the like. Also, the polypeptide encoded by the gene may be employed as a target of measurement. Although no particular limitation is imposed on the measurement target, so long as the target reflects the gene expression level, mRNA of the target gene is preferably employed as a measurement target. As used herein, the "measurement of gene expression level" also encompasses confirmation of the presence of expression of the gene.

Hereinafter, the PCR method will be described in detail. In the case where mRNA is employed as a measurement target, if required, the specimen is subjected to known preliminary treatments such as filtration, centrifugation, and chromatographic treatment. Then, RNA can be extracted from the specimen through a generally employed method such as the guanidine-cesium chloride ultracentrifugation method, the acidic guanidine-phenol chloroform method (AGPC method), the magnetic beads method, or the silica column method. RNA extraction may also be performed by means of a commercial kit (QIAGEN RNeasy Kit, TRIZOL, etc.).

The mRNA level may be determined through, for example, (1) determining the amount of the amplification product obtained through PCR employing a nucleic acid fragment which can specifically hybridize with the target mRNA and an RNA derived from the specimen; (2) determining the hybridization efficiency between a nucleic acid fragment which can specifically hybridize with the target mRNA and an RNA derived from the specimen; or (3) other known quantitation methods.

In the case of PCR, the "nucleic acid fragment which can specifically hybridize with the target mRNA" may be designed by comparing the nucleotide sequence of the target gene with the nucleotide sequence of another gene and selecting a sequence specific to mRNA of the target gene. The nucleotide sequence of mRNA of the target gene may be obtained with reference to, for example, a database (e.g., GenBank). Alternatively, the nucleotide sequence is aligned by means of a software (e.g., Clustal X), and a specific sequence is selected in a visual manner or the like. No particular limitation is imposed on the length of the nucleic acid fragment. However, a nucleic acid fragment consisting of 5 to 50 bases is preferred, with a nucleic acid fragment consisting of 18 to 25 continuous bases being more preferred.

The nucleic acid fragment which can hybridize with mRNA of the target gene is not limited to the thus-designed sequence, and those skilled in the art can appropriately conceive other equivalents on the basis of common technical sense. Such equivalents include a nucleic acid fragment having a nucleotide sequence complementary to the thus-designed sequence, and a nucleic acid fragment which has a nucleotide sequence homologous to any of the above sequences and which can be employed for determining the level of mRNA of the target gene. Examples of such equivalents include (a) a nucleic acid fragment which has a nucleotide sequence equivalent to the nucleotide sequence, except that 1 to 10, preferably 1 or several bases are substituted, added, or deleted; (b) a nucleic acid fragment which has a nucleotide sequence having an identity of 90% or higher, preferably 95% or higher, more preferably 99% or higher, to the nucleotide sequence; and (c) a nucleic acid fragment which has a nucleotide sequence which hybridizes, under stringent conditions, with the DNA fragment having a nucleotide sequence complementary to the nucleotide sequence.

The nucleic acid fragment may be a nucleic acid fragment in which any number, preferably 100 or less, more preferably 20 or less, even more preferably 10 or less of bases are added to one or two ends thereof, preferably to the 5' end.

The thus-designed nucleic acid fragment may be, for example, synthesized artificially, according to the nucleotide sequences thereof, by means of a DNA synthesizer. Preferably, the specificity of the nucleic acid fragment is confirmed after the synthesis. When the target mRNA is employed as a template, the specificity may be confirmed by the presence of a specific PCR amplicon, which is not obtained in the case of a certain reference.

In the case of ALAD gene, examples of such nucleic acid fragments include a nucleic acid fragment having a part of the nucleotide sequence defined by GenBank Accession No. NM_000031 or having a nucleotide sequence complementary to the nucleotide sequence, and a nucleic acid fragment which has a nucleotide sequence homologous to any of the above sequences and which is functionally equivalent to the above nucleic acid fragment. Examples of the nucleic acid fragment which has a nucleotide sequence homologous to any of the above sequences and which is functionally equivalent to the above nucleic acid fragment include the following nucleic acid fragments (a) to (c) which can be employed for determining the level of mRNA of the target gene. The same is applied to the cases of genes other than ALAD gene. Specific examples include (a) a nucleic acid fragment which has a nucleotide sequence equivalent to a part of the nucleotide sequence defined by GenBank Accession No. NM_000031 or a nucleotide sequence complementary to the nucleotide sequence, except that 1 or several bases are deleted, substituted, or added; (b) a nucleic acid fragment which has a nucleotide sequence having an identity of 90% or higher, preferably 95% or higher, more preferably 99% or higher, to a part of the nucleotide sequence defined by GenBank Accession No. NM_000031 or a nucleotide sequence complementary to the nucleotide sequence; and (c) a nucleic acid fragment which has a nucleotide sequence which hybridizes, under stringent conditions, with the DNA fragment having a part of the nucleotide sequence defined by GenBank Accession No. NM_000031 or a nucleotide sequence complementary to the nucleotide sequence.

The identity of a nucleotide sequence is calculated by means of a homology analysis program, GENETYX™.

The term "stringent conditions" refers to two DNA fragments being hybridized with each other under standard hybridization conditions as described by Sambrook J. et al. (Expression of cloned genes in *E. coli* (Molecular Cloning: A laboratory manual (1989)), Cold Spring Harbor Laboratory Press, New York, USA, 9.47-9.62 and 11.45-11.61).

The mRNA level of a specimen may be determined through PCR employing the thus-produced nucleic acid fragments and RNA derived from the specimen, preferably through real-time RT-PCR including a step of producing cDNA from mRNA. RT-PCR may be performed according to a known technique such as two-step RT-PCR or one-step RT-PCR. From the viewpoints of simplicity and prevention of cross-contamination, one-step RT-PCR is preferred. One-step RT-PCR may be performed by means of, for example, a commercial kit (e.g., QIAGEN One-Step RT-PCR kit). As the enzyme having reverse transcription activity which may be employed in RT reaction, a variety of reverse transcriptases such as MMLV reverse transcriptase may be employed. The DNA polymerase, which is employed in PCR for amplifying a DNA fragment, preferably has heat resistance ($\geq 90°$ C.).

In one mode of such PCR, thermal denaturation reaction (double strand DNA to single strand DNA) is performed at 90 to 98° C., annealing reaction for hybridizing a primer to template cDNA is performed at 37 to 72° C., and extension reaction in which DNA polymerase acts is performed at 50 to 75° C. The set of reactions (cycle) is performed once to some tens of times. One preferred reaction conditions include thermal denaturation at 95° C. for 30 seconds, annealing at 60° C. for 30 seconds, and extension at 72° C. for 40 seconds. In PCR, two primers are preferably used in combination. In this case, the two primers must be selected so as to form a combination of a sense strand and an anti-sense strand. The nucleic acid fragment of the present invention may serve as a probe, and may be used in combination with other known universal primers, oligonucleotides, etc.

The specimen sample containing mRNA serving as a template for RT-PCR preferably has a total RNA amount of 1 pg to 1 μg, more preferably 2 ng to 50 ng.

When PCR has appropriately proceeded, the "PCR amplicon amount" and the "PCR cycle number" are generally correlated with the "PCR template amount." Thus, the mRNA level of a target gene; i.e., the target gene expression level, can be calculated from the amount of amplicon produced in PCR and the PCR cycle number.

No particular limitation is imposed on the method of determining the PCR amplicon amount and the PCR cycle number, and any method may be employed. For example, the PCR cycle number may be counted when the DNA level has reached a predetermined level. This procedure may be performed by, for example, determining the PCR cycle number when the fluorescence intensity has reached a predetermined level in a combinatory method including the PCR method in which a PCR amplicon is labeled and the PCR method in which the label is monitored with time. In one typical procedure, the labeling is performed by use of a fluorescent dye, and the label is monitored by measuring fluorescence intensity. In one mode of labeling with a fluorescent dye, an intercalater fluorescent dye such as SYBR(R) Green I may be employed. Since the intercalater fluorescent dye enhances the fluorescence intensity via intercalation with a double-strand nucleic acid, a fluorescence intensity which correctly reflects the PCR amplicon level is obtained. Labeling with a fluorescent dye may also be accomplished by use of TaqMan probe, Moleculer Beacon, etc., which are labeled with a fluorescent dye. A TaqMan probe or Moleculer Beacon is a probe in which a fluorescent dye and a quencher are bonded to an oligonucleotide having a homology to an internal sequence of a region which is amplified through PCR. The probe is additionally employed in PCR. Since fluorescence in response to the degree of PCR is emitted through interaction between the fluorescent dye and the quencher bonded to the probe, the PCR product formed through amplification can be monitored by measuring the fluorescence intensity at each PCR stage.

As described above, the target gene mRNA level of a specimen may also be determined from, for example, the hybridization efficiency between the nucleic acid fragment which can hybridize specifically with a target mRNA and RNA derived from the specimen.

The nucleic acid fragment which can hybridize specifically with a target gene mRNA may be a nucleic acid fragment as designed and produced in the aforementioned manner. The nucleic acid fragment is preferably a labeled nucleic acid fragment. Examples of the labeling agent include an enzyme, a paramagnetic ion, biotin, a fluorescent dye, a chromophore, a heavy metal, and a radio-isotope. A more preferred is an enzyme. Examples of the enzyme include horse radish peroxidase and alkaline phosphatase. The labeling may be performed through a known method. Through determining the hybridization degree between a sample containing RNA derived from a specimen and the nucleic acid fragment, the target gene mRNA level of the specimen can be determined through a known calculation method. No particular limitation is imposed on the method of determining the degree of hybridization, and it may be determined according to a known method, for example, measuring a label bound to the nucleic acid fragment. That is, when a nucleic acid fragment labeled with a fluorescent dye is used, the fluorescence intensity is measured, for determining the degree of hybridization.

The expression level of a target gene may also be determined by use, as a probe, of a nucleic acid fragment which can specifically hybridize with a nucleotide sequence of the target gene or mRNA thereof. In the case of ALAD gene, there may be used, as a probe, a nucleic acid fragment having a part of the nucleotide sequence defined by GenBank Accession No. NM_000031 (e.g., GAGGAGTCCCCAGCTATTGAG-GCAA) (SEQ ID NO: 1) or having a nucleotide sequence complementary to the nucleotide sequence, or a nucleic acid fragment which has a nucleotide sequence homologous to any of the above sequences and which is functionally equivalent to the above nucleic acid fragment. These probes may be immobilized on any solid phase, to thereby provide a DNA chip, a gene chip, a cDNA microarray, an oligo DNA array, etc.

Other than the aforementioned probes, there may also be employed, as a probe, a combination of a plurality of nucleic acid fragments which are designed to specifically detect a nucleotide sequence of the target gene or mRNA thereof and which can specifically hybridize with plurality of regions appropriately selected from a nucleotide sequence of the target gene or mRNA thereof.

No particular limitation is imposed on the solid phase which is employed for immobilizing a probe, so long as the solid phase can immobilize polynucleotide. Examples of the solid phase include glass plate, nylon membrane, microbeads, a silicon chip, and a capillary. The solid phase may be labeled. No particular limitation is imposed on the labeling agent, and a fluorescent dye, a radio-isotope, etc. may be used. In immobilization of polynucleotide on a solid phase, a polynucleotide which has been synthesized in advance may be placed on a solid phase, or a target polynucleotide may be synthesized on a solid phase. When a DNA microarray is selected, immobilization may be performed by use of a commercial spotter or the like, through an appropriate known method (printing polynucleotide through ink-jet method, in situ synthesis, or photolithography) depending on the type of the probe to be immobilized.

The expression level of a target gene may be determined by hybridizing the above-prepared DNA chip or the like with a labeled DNA or RNA prepared from an RNA obtained from a specimen (e.g., cultured cells, tissue, tissue section, or blood lysate) or a labeled DNA or RNA prepared directly from the specimen; and measuring, as a signal attributed to the labeled probe, the amount of the double-strand formed of the probe and the labeled DNA or RNA. The signal may be detected through a routine method, for example, by means of a radiation counter, a fluorescence detector, etc.

Alternatively, the expression level of a target gene may be determined through the microbeads method. For example, the expression levels of a plurality of target genes can be simultaneously determined through the following procedure. Specifically, probes for mRNA derived from different target genes are immobilized on microbeads which have been labeled with different fluorescent agents. The mRNA of the target genes prepared from a specimen (e.g., cultured cells, tissue, tissue section, or blood lysate) are hybridized therewith, and each target gene is specifically detected through the fluorescence therefrom. Also, a labeled probe is hybridized with mRNA of target genes which have hybridized with the probes immobilized on the microbeads, and the label of the probe is detected, to thereby determine the mRNA levels.

Furthermore, the copy number and the expression level of a target gene may be determined by use of the aforementioned probe through a known method (e.g., the southern hybridization method, the northern hybridization method, the FISH method, or the CGH method). In the case where a polypeptide encoded by the target gene is measured, the expression level of the target gene may be determined through a known immunostaining method (the ELISA method, the western blotting method, the EIA method, the RIA method, the IHC method, or the like) employing an antibody specific to the polypeptide.

In determination of the sensitivity of a subject to an anti-cancer agent, the expression levels of the target genes in a biological sample collected from a cancer patient before or during administration of the anti-cancer agent are measured. In the case where the target genes are CABLES1 gene, GDA gene, HOXB6 gene, and TMEM18 gene, when the obtained value of expression levels is equal to or higher than a predetermined reference value, the cancer has no sensitivity to the anti-cancer agent, whereas when the obtained value is lower than the reference value, the cancer has sensitivity to the anti-cancer agent.

Furthermore, the best tumor response (ratio) of the cancer patient is calculated from the expression levels of five genes; ALAD gene, C20orf43 gene, GDA gene, TMEM18 gene, and UGT2B10 gene, by formula (1). When the obtained value is equal to or higher than a predetermined reference value, the cancer has sensitivity to the anti-cancer agent, whereas when the obtained value is lower than the reference value, the cancer has no sensitivity to the anti-cancer agent. The predetermined reference value may be appropriately modified in accordance with the conditions and cancer type of the target cancer patient, the type of a drug including an additional anti-cancer agent employed in combination with an anti-cancer agent containing oxaliplatin or a salt thereof, fluorouracil or a salt thereof, and levofolinate or a salt thereof, etc. (see the Examples hereinbelow). In the case where fluorouracil, levofolinate, and oxaliplatin are administered in combination, for example, the reference value of the best tumor response (ratio) is preferably 0.5 or higher, particularly preferably 0.7 or higher.

Before administration of an anti-cancer agent, when the expression level of each gene denies sensitivity, or when the value obtained by the formula (1) is lower than the reference value, the cancer can be found to have no sensitivity to the anti-cancer agent. In this case, the effect of the agent is not expected. If such an ineffective anti-cancer agent is continuously administered to a cancer patient, progression of the cancer and aggravation of adverse effects may be anticipated. Thus, the sensitivity determination method of the present invention greatly contributes not only to determination of possible therapeutic response provided by an anti-cancer agent but also to prevention of aggravation of adverse effects which would otherwise be caused by continuous administration of an ineffective anti-cancer agent. Particularly, the sensitivity determination method of the present invention can be suitably applied to a cancer patient before administration of an anti-cancer agent. In addition, the method can also be employed as a method for actively selecting a patient who is expected to be treated by an anti-cancer agent.

Through measuring the expression levels of the target genes in a biological sample derived from a cancer patient who is currently receiving an anti-cancer agent and monitoring the expression level of each of the genes or the values obtained from the formula (1) at every therapy cycle, the sensitivity of the cancer to the anti-cancer agent can be evaluated with time, whereby the method may also serve as a method for determining whether or not the therapy is to be continued. When the cancer has no sensitivity to the anti-cancer agent, a pharmaceutical effect of the agent is no longer expected, and only adverse effects of the anti-cancer agent are conceivably provided. Thus, the sensitivity determination method of the present invention may also be employed for preventing onset of undesired adverse effects and progression of cancer and aggravation of adverse effects which would otherwise be caused by continuation of ineffective therapy.

In addition to best tumor response (ratio), there may also be employed as a parameter for the sensitivity determination, efficacy-related parameters such as overall survival (days), progression-free survival (days), duration of overall response (days), duration of stable disease (days), and time to treatment failure (days), and adverse effect-related parameters such as the blood concentration, elimination half-life, bioavailability, area under the blood concentration time curve, clearance, distribution volume, etc. of the anti-cancer agent and a metabolite thereof.

No particular limitation is imposed on the additional anti-cancer agent used in combination with oxaliplatin or a salt thereof, fluorouracil or a salt thereof, and levofolinate or a salt thereof. Examples of the additionally used anti-cancer agent include cyclophosphamide, ifosfamide, thiotepa, melphalan, busulfan, nimustine, ranimustine, dacarbazine, procarbazine, temozolomide, cisplatin, carboplatin, nedaplatin, methotrexate, pemetrexed, tegaful/uracil, doxifluridine, tegaful/gimeracil/oteracil, capecitabine, cytarabine, enocitabine, gemcitabine, 6-mercaptopurine, fuludarabin, pentostatin, cladribine, hydroxyurea, doxorubicin, epirubicin, daunorubicin, idarubicine, pirarubicin, mitoxantrone, amurubicin, actinomycin D, bleomycin, pepleomycin, mytomycin C, aclarubicin, zinostatin, vincristine, vindesine, vinblastine, vinorelbine, paclitaxel, docetaxel, irinotecan, active metabolite of irinotecan (SN-38), nogitecan (topotecan), etoposide, prednisolone, dexamethasone, tamoxifen, toremifene, medroxyprogesterone, anastrozole, exemestane, letrozole, rituximab, imatinib, gefitinib, gemtuzumab ozogamicin, bortezomib, erlotinib, cetuximab, bevacizumab, sunitinib, sorafenib, dasatinib, panitumumab, asparaginase, tretinoin, arsenic trioxide, a salt of any of these, and an active metabolite thereof. Of these, irinotecan, SN-38, a salt of any of these, and bevacizumab are preferred, with bevacizumab being particularly preferred.

In carrying out the method of the present invention for determining the sensitivity of a subject to an anti-cancer agent, there is preferably employed a kit containing a protocol for determining expression levels of one or more genes in a specimen selected from the group consisting of ALAD gene, C20orf43 gene, CABLES1 gene, CDC14B gene, GDA gene, HOXB6 gene, RPL7AP27 gene, TMEM18 gene, and UGT2B10 gene. The protocol for determining gene expression levels includes, for example, a protocol which indicates the method for determining the expression level of a target gene, a reagent used in the method for determining the expression level of the target gene, and a DNA chip in which a nucleic acid fragment which can hybridize specifically with the mRNA of the target gene has been immobilized. In addition, the kit may further contain reference values for determining whether or not the subject has sensitivity to the anti-cancer agent. The reference values include standard expression level of respective genes, expression levels which are evaluated as high levels, expression levels which are evaluated as low levels, and the factors (and the degree of factors) of affecting the expression levels. These reference values may be appropriately predetermined separately in accordance with the conditions of target cancer patient, the type of specimen, the type of cancer, the type of the drug including an additional anti-cancer agent used in combination with an anti-cancer agent containing oxaliplatin or a salt thereof, fluorouracil or a salt thereof, and levofolinate or a salt thereof, and the parameters for determining the sensitivity. With reference to the reference values, sensitivity determination can be carried out in a manner as described above.

In the case where the best tumor response (ratio) is calculated from the expression levels of five genes; ALAD gene, C20orf43 gene, GDA gene, TMEM18 gene, and UGT2B10 gene, by the aforementioned formula (1), the sensitivity determination kit contains (A) a protocol for determining expression levels of the aforementioned five genes and (B) a protocol for calculating the best tumor response (ratio). The protocol (A) for determining expression levels of the aforementioned five genes contains, for example, (A1) a protocol which indicates the method for determining the expression level of a target gene, (A2) a reagent used in the method for determining the expression level of the target gene, and (A3) a DNA chip in which a nucleic acid fragment which can hybridize specifically with the mRNA of the target gene has been immobilized. The protocol (B) contains (B1) a protocol for calculating the best tumor response (ratio) by formula (1) and (B2) reference values for determining whether or not the subject has sensitivity to the anti-cancer agent or the like. The reference values include standard values of best tumor response (ratio), and the factors (and the degree of factors) of affecting the standard values. These reference values may be appropriately predetermined in accordance with the conditions of target cancer patient, the type of specimen, the type of cancer, and the type of the drug including an additional anti-cancer agent used in combination with an anti-cancer agent containing oxaliplatin or a salt thereof, fluorouracil or a salt thereof, and levofolinate or a salt thereof. With reference to the reference values, sensitivity determination can be carried out in a manner as described above.

The kit of the present invention is not limited to the above embodiments and encompasses a kit including all or a part of the members required for carrying out all or a part of the steps of the method. Examples of "members required for carrying out the steps" include a buffer.

When a variation in expression of one or more genes selected from the group consisting of ALAD gene, C20orf43 gene, CABLES1 gene, CDC14B gene, GDA gene, HOXB6 gene, RPL7AP27 gene, TMEM18 gene, and UGT2B10 gene in a specimen is employed as an index, a sensitivity-enhancing agent to an anti-cancer agent can be selected through screening.

Specifically, in the case where the target genes are CABLES1 gene, GDA gene, HOXB6 gene, and TMEM18 gene, a sensitivity-enhancing agent to an anti-cancer agent can be selected through screening by employing, as an index, suppression of the expression of the genes. In other words, the substance which suppresses the expression of the genes in vitro or in vivo enhances sensitivity of a subject to an anti-cancer agent. For example, in a cancer animal, the substance which promotes suppression of gene expression before and after administration of an anti-cancer agent is defined as a substance which enhances the sensitivity to the anti-cancer agent (anti-cancer agent sensitivity-enhancing agent). In various cancer cell lines, the substance which promotes suppression of gene expression in vitro in the presence of an anti-cancer agent is defined as a substance which enhances the sensitivity to the anti-cancer agent (anti-cancer agent sensitivity-enhancing agent).

By employing, as an index, an increase in the best tumor response (ratio) obtained from the formula (1), a sensitivity-enhancing agent to an anti-cancer agent can be selected through screening. In other words, the substance which increases the value in vitro or in vivo enhances sensitivity of a subject to an anti-cancer agent. For example, in a cancer animal, the substance which promotes rise in the value before and after administration of an anti-cancer agent is defined as a substance which enhances the sensitivity to the anti-cancer agent (anti-cancer agent sensitivity-enhancing agent). In various cancer cell lines, the substance which promotes rise in the value in vitro in the presence of an anti-cancer agent is defined as a substance which enhances the sensitivity to the anti-cancer agent (anti-cancer agent sensitivity-enhancing agent).

When an anti-cancer agent sensitivity-enhancing agent is used, a variation in expression of each gene or an increase in the value obtained from the aforementioned formula (1) is observed before observation of regression of the tumor or cytocidal effect. Therefore, whether or not the test substance can serve as a useful anti-cancer agent sensitivity-enhancing agent can be determined in a shorter period of time, whereby load and cost involved in screening can be reduced, which is a great advantage of the present invention.

Through employment of the thus-obtained anti-cancer agent sensitivity-enhancing agent and an anti-cancer agent of interest (sensitivity enhancement target) in combination, the therapeutic effect of the anti-cancer agent can be remarkably enhanced. The composition of the present invention may be administered orally or parenterally. Upon administration, a composition containing an anti-cancer agent sensitivity-enhancing agent and an anti-cancer agent (sensitivity enhancement target) may be mixed with a solid or liquid non-toxic pharmaceutical carrier for providing a formulation suited for the administration route (oral, intrarectal, injection, etc.), to thereby form a general pharmaceutical preparation. The composition containing an anti-cancer agent sensitivity-enhancing agent and an anti-cancer agent (sensitivity enhancement target) may be a single composition containing both ingredients or a combination-type composition of a plurality of preparations. These ingredients may be administered through different routes.

Examples of the form of preparations include solid formulations such as tablet, granules, powder, and capsule; liquid preparations such as solution, suspension, and emulsion; and lyophilized formulations. These preparations may be produced through a method generally employed in the art. Examples of the non-toxic pharmaceutical carrier include starch, dextrin, fatty acid glyceride, polyethylene glycol, hydroxyethyl starch, ethylene glycol, polyoxyethylene sorbitan fatty acid ester, amino acid, gelatin, albumin, water, and physiological saline. If required, additives generally employed in the art such as a stabilizer, a humectant, an emulsifying agent, a binder, a tonicity agent, and a vehicle (diluent) may be appropriately added to the composition.

Note that the value of the first term and the factor of each gene expression level in the formula (1) were determined from the data of gene expression levels obtained through real-time RT-PCR. However, if gene expression levels obtained through real-time RT-PCR have a certain correlation with those obtained through a method other than real-time RT-PCR, the value of the first term and the factor of each gene expression level in the formula (1) may be modified with certain factors which adjust variations between real-time RT-PCR and a method other than real-time RT-PCR, and the thus-adjusted formula may be used. In this case, gene expression levels determined through a method other than real-time RT-PCR are input into the relevant formula. Even when real-time RT-PCR is employed, respective gene expression levels slightly vary depending on the condition and number of the target cancer patients, the type of cancer, the type of a drug including an additional anti-cancer agent used in combination with an anti-cancer agent containing oxaliplatin or a salt thereof, fluorouracil or a salt thereof, and levofolinate or a salt thereof, and other factors. In such a case, an additional factor for modifying the first term and the factor of each gene expression level is added to the formula (1), and the thus-modified formula (1) may be employed.

EXAMPLES

The present invention will next be described in more detail by way of examples, which should not be construed as limiting the invention thereto.

Studies by Clinical Test of Human Subjects Received mFOL-FOX6 Regimen

1. Clinical Test of Human Subject Who Had Received mFOL-FOX6 Regimen

The tested human subjects were cancer patients who had received a cancer chemotherapy (mFOLFOX6) involving administration, in combination, fluorouracil (400 mg/m$^2$) (via rapid intravenous injection), levofolinate (200 mg/m$^2$), fluorouracil (2,400 to 3,000 mg/m$^2$) (via continuous intravenous infusion), and oxaliplatin (85 mg/m$^2$). In order to identify and confirm the genes relating to the effect of cancer chemotherapy, prospective genomic pharmacological clinical studies were carried out. The target cases were unresectable stage IV colorectal cancer patients who had not received chemotherapy and from whom a tumor specimen could be removed during palliative surgery. The selection criteria for the test human subjects were as follows: (1) a case which was histologically diagnosed as colorectal cancer; (2) a case which underwent surgery of unresectable stage IV colorectal cancer; (3) a case involving response evaluation criteria in solid tumors (RECIST); and (4) a case where physiological functions (bone marrow, liver, kidney, heart, etc.) are sufficiently maintained, wherein the blood test results within one week before preliminary registration or registration fell within the following reference ranges: WBC: 4,000/μL to 12,000/μL, NEUT: ≥2,000/μL, PLT: ≥100,000/μL, Hb: ≥9.0 g/dL, serum AST•ALT: not more than twice the upper limit of normal at the institution (in the case of liver metastasis, not more than three times), T-Bil: ≤1.5 mg/dL, Cr: ≤1.5 mg/dL, CCr: ≥50 mL/min, BUN: ≤25 mg/dL, and CRP ≤1 mg/dL. The test human subjects also included a case classified in performance status (Eastern Cooperative Oncology Group: ECOG) of 0 to 2; a case which underwent no preliminary treatment other than surgery; a case for which, at registration, 21 days or longer had passed after surgery; a case which is expected to have a predicted survival period of 3 months or longer; a case which has no severe co-morbidity or active multiple primary cancer; a case of an age of 20 or older and younger than 75; a case from which a tissue sample for gene analysis was obtained at surgery; and a case where a patient himself or herself provided informed consent of surgery including donation of a biological sample for studies. Excluded were the following cases: (1) a case having a severe complication; (2) a case having an infectious complication; (3) a case having diarrhea (watery stools); (4) a case having intestinal paralysis, ileus, or subileus (only before registration); (5) a case having interstitial pneumonia or pulmonary fibrosis; (6) a case having ascites or pleural fluid in a large volume; (7) a case having jaundice; (8) a case having a heart disease such as ischemic heart disease or arrythmia to an extent requiring treatment (a case having left ventricular hypertrophy or slight left ventricular overload concomitant with hypertension or slight right bundle branch block may be registered); (9) a case which experienced heart infarction within 6 months; (10) a case having cirrhosis as a complication; (11) a case exhibiting fresh hemorrhage from the digestive tract to be treated by repeated blood transfusion; (12) a case having a mental disorder treated with or possibly to be treated with a psychotropic; (13) a case having difficult-to-control diabetes as a complication; (14) a case having other severe post-operative complications; (15) a case experienced severe anaphylaxis to other drugs; (16) a female subject in pregnancy or lactation or a male or female subject wishing to have a baby; and (17) a case which is positive to hepatitis virus, HIV virus, or syphilis. In the mFOLFOX6 regimen, administration was started ≤28 days after surgical operation. From day 1 (administration starting day), administration was performed once a week for one week, followed by a one-week rest period, in two weeks as 1 course.

Fifty-six subjects in total participated in the study, and 54 subjects of them could be evaluated in terms of tumor response of a target lesion. Among the 54 subjects, four cases (reference cases) who exhibited a test score falling outside the above ranges were excluded, and RNA for evaluating gene expression levels was obtained from 44 cases. Among 44 cases, genes relating to the sensitivity to an anti-cancer agent therapy were retrieved from 37 cases who were adapted to DNA microarray analysis.

As a DNA microarray, Whole Human Genome 4×44K (product of Agilent) was used. DNA microarray analysis was performed by the following steps; (1) synthesis of cDNA from total RNA, (2) synthesis of labeled cRNA from cDNA, (3) fragmentation of cRNA, (4) hybridization of fragmented cRNA with microarray, (5) washing of the microarray, (6) scanning of the microarray, and (7) gene expression analysis, in this order.

Total RNA was extracted from human colorectal cancer tissue samples of 54 cases by means of RNeasy™ Mini kit (product of Qiagen) according to a protocol attached thereto, and each RNA sample was stored at −80° C.

(1) Synthesis of cDNA from Total RNA

Double-strand cDNA was synthesized by means of Quick Amp Labeling Kit (product of Agilent) according to a protocol attached thereto. Specifically, total RNA (500 ng) was diluted with nuclease-free water to 5.3 μL, and the dilute was mixed with T7 promoter primer (1.2 μL) contained in the kit and diluted Spike-Mix (product of Agilent) (5 μL) as a positive control. The mixture (total volume: 11.5 μL) was heated at 65° C. for 10 minutes and then cooled on ice for 5 minutes. Under cooling on ice, 5× first-strand buffer (4 μL), 10 mM dNTP mix (1 μL), 0.1 M DTT (2 μL), RNase inhibitor (0.5 μL), and MMLV reverse transcriptase (1 μL), which were components of the kit, were added to the mixture. The resultant mixture (total volume 20 μL) was heated at 40° C. for 2 hours and further at 65° C. for 15 minutes in order to terminate cDNA synthesis reaction. After termination of the reaction, the reaction mixture was cooled on ice for 5 minutes.

(2) Synthesis of Labeled cRNA from cDNA

Subsequently, in vitro transcription (IVT) was performed by means of Quick Amp Labeling Kit (product of Agilent) according to a protocol attached thereto, to thereby synthesize cRNA. Specifically, 4×transcription buffer (20 μL), 0.1 M DTT (6 μL), NTP mix (8 μL), 50% PEG (6.4 μL), RNase inhibitor (0.5 μL), inorganic pyrophosphatase (0.6 μL), T7 RNA polymerase (0.8 μL), cyanine 3-CTP (2.4 μL), and nuclease-free water (15.3 μL), which were components of the kit, were sufficiently mixed together. The mixture (total volume: 60 μL) was added to the cDNA solution (20 μL) prepared in (1), and the resultant mixture was heated at 40° C. for 2 hours. After completion of reaction, the reaction mixture was purified by means of RNeasy Mini Kit (product of Qiagen) according to a protocol attached thereto, to thereby yield purified cRNA. More specifically, nuclease-free water (20 μL) was added to the reaction mixture (80 μL), and to the resultant solution (total volume: 100 μL), BufferRLT (350 μL) contained in the kit was added, followed by sufficient mixing. To the mixture, 100% ethanol (250 μL) was added, followed by sufficient mixing. The resultant mixture (total volume: 700 μL) was added to RNeasy mini-spin column contained in the kit and centrifuged at 13,000 rpm for 30 seconds. The RNeasy mini-spin column was set into a new 2-mL tube. Buffer RPE (500 μL) contained in the kit was added to the column, and the resultant was centrifuged at 13,000 rpm for 30 seconds, to thereby remove elution liquid.

The mini-spin column was set again into the 2-mL tube, and Buffer RPE (500 µL) was added to the column. The resultant was centrifuged at 13,000 rpm for 1 minute, to thereby remove elution liquid. The mini-spin column was transferred to a new 1.5-mL tube, and nuclease-free water (30 µL) was added directly to the membrane. The tube was allowed to stand at room temperature for 1 minute and then subjected to centrifugation at 13,000 rpm for 30 seconds, to thereby elute a cRNA sample.

cRNA was quantitated by means of NanoDrop (product of Thermo scientific). The absorbance of the sample solution was measured at 260 nm and 280 nm, to thereby determine cRNA concentration and confirm that the percent Cy3-CTP dye incorporation was ≥9 pmol/µg. The quality of cRNA was investigated by means of Agilent 2100 Bioanalyzer according to a protocol attached thereto. Specifically, the smear peak was found to have a length of ≥500 bases in electrophoresis.

(3) Fragmentation of cRNA cRNA was fragmented by means of Gene Expression Hybridization Kit (product of Agilent) according to a protocol attached thereto. Specifically, cRNA (1.65 µg) was diluted with nuclease-free water so as to adjust the volume to 41.8 µL. 25×fragmentation buffer (2.2 µL) and 10×blocking agent (11 µL), which were components of the kit, were added to the diluted cRNA, and the mixture was heated at 60° C. for 30 minutes, followed by cooling on ice for 1 minute. To the solution containing cRNA fragments (55 µL), 2×hybridization Buffer HI-RPM (55 µL) contained in the kit was added, to thereby prepare a hybridization solution (total volume: 110 µL).

(4) Hybridization of Fragmented cRNA with Microarray

The hybridization was performed by means of a hybridization oven (product of Agilent) and a hybridization rotor (product of Agilent) according to a protocol attached thereto. Specifically, the hybridization solution prepared in (3) was applied to a Whole Human Genome 4×44K array surface, and the array surface was covered with a gasket slide (product of Agilent). The array was fixed by means of a hybridization chamber for oligo-DNA microarray (product of Agilent). The thus-fixed array was set in a hybridization rotor and heated in a hybridization oven at 65° C. for 17 hours under rotation at 10 rpm.

(5) Washing of Microarray

After completion of hybridization, the microarray fixed by the hybridization chamber for oligo-DNA microarray was removed from the chamber and washed. Specifically, the microarray was transferred into a reservoir filled with a Gene Expression Wash Buffer 1 (product of Agilent) containing 0.005% Triton X-102, and washed under stirring with a stirrer bar at room temperature for 1 minute. Then, the washed microarray was transferred into a thermostat bath equipped with a stirrer filled with a Gene Expression Wash Buffer 2 (product of Agilent) containing 0.005% Triton X-102, and washed under stirring with a stirrer bar at 37° C. for 1 minute.

(6) Scanning of Microarray

The thus-washed microarray was set in a slide holder and subjected to scanning by means of an Agilent G2565BA scanner (product of Agilent), whereby a fluorescence pattern was read out. The data were stored as a TIFF image. The TIFF image was processed by software; Agilent Feature Extraction Ver. 9.5, whereby signal intensities of the spots observed on the array attributed to respective genes were calculated.

(7) Gene Expression Analysis

In the gene expression analysis, the thus-obtained signal intensity data were normalized by gene expression analysis software; GeneSpring GX (product of Agilent). Specifically, a background signal was subtracted from each spot signal. When the difference was less than 0.01, the difference was employed as 0.01. The value was divided by a ¾ height value of signals of all the spots in the array and converted to a logarithm (base: 2), to thereby provide a normalized relative gene expression level.

2. Retrieval of Sensitivity-Related Genes

From the results of analysis of 37 cases which were able to be analyzed through DNA microarray analysis, genes which can predict best tumor response (ratio) were retrieved. The correlation of the results of DNA microarray analysis of the 37 cases with best tumor response was investigated through Pearson's product-moment correlation analysis and Spearman's rank correlation analysis. As a result, 17 genes were identified as genes which had an absolute value of correlation factor R of more than 0.5, a p value of less than 0.2 as obtained by the test of correlation factor ρ, and a relative mean expression level of more than 0.5 (Table 1). Also, the same analysis was performed with respect to 41 cases, including 4 additional reference cases. As a result, 10 genes were identified as genes which had an absolute value of correlation factor R of more than 0.5, a p value of less than 0.05 as obtained by the test of correlation factor ρ, and a relative mean expression level of more than 0.5 (Table 2). Among the 17 genes selected from the analysis results of 37 cases and the 10 genes selected from the analysis results of 41 cases, 9 common genes belonging to both groups were identified (Table 3). Since these 9 genes were commonly identified in both groups analyzed under different conditions, these genes were considered to be more clinically useful. Thus, the correlation between each of the nine genes and the best tumor response was evaluated.

TABLE 1

| Gene symbol | Gene name |
| --- | --- |
| ALAD | aminolevulinate, delta-, dehydratase |
| C20orf43 | chromosome 20 open reading frame 43 |
| CABLES1 | Cdk5 and Abl enzyme substrate 1 |
| CDC14B | CDC14 cell division cycle 14 homolog B (S. cerevisiae) |
| FAM73B | family with sequence similarity 73, member B |
| ARHGEF40 | Rho guanine nucleotide exchange factor (GEF) 40 |
| GAL3ST1 | galactose-3-O-sulfotransferase 1 |
| GDA | guanine deaminase |
| HOXB6 | homeobox B6 |
| KIF26A | kinesin family member 26A |
| LOC100133121 | hypothetical protein LOC100133121 |
| RPL7AP27 | ribosomal protein L7a pseudogene 27 |
| MAOA | monoamine oxidase A |
| TMEM18 | transmembrane protein 18 |
| TRIM32 | tripartite motif-containing 32 |
| UGT2B10 | UDP glucuronosyltransferase 2 family, polypeptide B10 |
| WDR5 | WD repeat domain 5 |

TABLE 2

| Gene symbol | Gene name |
| --- | --- |
| ACYP | acylphosphatase 1, erythrocyte (common) type |
| ALAD | aminolevulinate, delta-, dehydratase |
| C20orf43 | chromosome 20 open reading frame 43 |
| CABLES1 | Cdk5 and Abl enzyme substrate 1 |
| CDC14B | CDC14 cell division cycle 14 homolog B (S. cerevisiae) |
| GDA | guanine deaminase |
| HOXB6 | homeobox B6 |
| RPL7AP27 | ribosomal protein L7a pseudogene 27 |
| TMEM18 | transmembrane protein 18 |
| UGT2B10 | UDP glucuronosyltransferase 2 family, polypeptide B10 |

TABLE 3

| Gene symbol | Gene name |
|---|---|
| ALAD | aminolevulinate, delta-, dehydratase |
| C20orf43 | chromosome 20 open reading frame 43 |
| CABLES1 | Cdk5 and Abl enzyme substrate 1 |
| CDC14B | CDC14 cell division cycle 14 homolog B (*S. cerevisiae*) |
| GDA | guanine deaminase |
| HOXB6 | homeobox B6 |
| RPL7AP27 | ribosomal protein L7a pseudogene 27 |
| TMEM18 | transmembrane protein 18 |
| UGT2B10 | UDP glucuronosyltransferase 2 family, polypeptide B10 |

In order to investigate the correlation between each of the thus-identified 9 genes and the best tumor response, the expression levels of respective genes were determined through real-time RT-PCR employing TaqMan™ Gene Expression Assays, and the results were evaluated by regression analysis. Table 4 shows the results. RPL7AP27 gene was excluded from the analysis targets, since a primer probe of the gene suited for RT-PCR could not be produced.

TABLE 4

| Gene symbol | Coefficient of determination ($R^2$) | p Value |
|---|---|---|
| ALDA | $4.672 \times 10^{-8}$ | 0.9989 |
| C20orf43 | 0.001672 | 0.7921 |
| CABLES1 | 0.02095 | 0.3486 |
| CDC14B | 0.01693 | 0.3999 |
| GDA | 0.1029 | 0.03374 |
| HOXB6 | 0.03243 | 0.2421 |
| TMEM18 | 0.03278 | 0.2395 |
| UGT2B10 | 0.009458 | 0.53 |

The data of the expression level of each gene were classified into two groups; a high expression level group and a low expression level group, and each group was analyzed through the t-test. Table 5 shows the results. RPL7AP27 gene was excluded from the analysis targets, since a primer probe of the gene suited for RT-PCR could not be produced.

TABLE 5

| Gene symbol | p Value |
|---|---|
| ALDA | 0.9204 |
| C20orf43 | 0.3236 |
| CABLES1 | 0.826 |
| CDC14B | 0.4518 |
| GDA | 0.04124 |
| HOXB6 | 0.8637 |
| TMEM18 | 0.06296 |
| UGT2B10 | 0.2854 |

The data of best tumor response were classified into a CR+PR group and an SD+PD group, in accordance with the RECIST standards, and each group was analyzed through the t-test. Also, the data were classified into a CR+PR group, an SD group, and a PD group, and each group was analyzed through one-way analysis of variance. Table 6 shows the results. The expression levels of CABLES1 gene, GDA gene, HOXB6 gene, and TMEM18 gene were found to be statistically higher in the SD+PD group (no response to the therapy) than in the CR+PR group (with response to the therapy). RPL7AP27 gene was excluded from the analysis targets, since a primer probe of the gene suited for RT-PCR could not be produced.

TABLE 6

| | t Test | Analysis of variance | |
|---|---|---|---|
| Gene symbol | p Value | F Value | p Value |
| ALAD | 0.839 | 0.6462 | 0.5293 |
| C20orf43 | 0.3109 | 1.4031 | 0.2574 |
| CABLES1 | 0.06737 | 2.8439 | 0.06973 |
| CDC14B | 0.3612 | 0.5241 | 0.596 |
| GDA | 0.03838 | 2.2336 | 0.12 |
| HOXB6 | 0.02316 | 3.193 | 0.05143 |
| TMEM18 | 0.04377 | 2.2318 | 0.1202 |
| UGT2B10 | 0.159 | 1.5994 | 0.2144 |

3. Establishment and Verification of a Sensitivity-Predicting Formula

Through the above studies, among the 9 sensitivity-related genes identified by use of a DNA microarray, the 8 genes excepting RPL7AP27 gene each were found to have a statistically significant correlation with sensitivity to an anti-cancer agent. Also, the 8 genes were analyzed through multiple regression analysis, and a formula predicting best tumor response by inputting the expression levels of the identified genes was established. The predictability of the formula was verified. The aforementioned 44 cases in which RNA required for evaluating the expression levels had been obtained were divided into a study group (26 cases, employed for establishing a prediction formula) and a verification group (18 cases, employed for verifying the prediction formula). The expression levels of the 8 genes were determined through real-time RT-PCR. By use of the expression levels of the 8 genes of the study group (26 cases), a formula predicting best tumor response was established through multiple regression analysis. Thus, as the formula which can most correctly predict the best tumor response, the following formula including expression levels of 5 genes (ALAD gene, C20orf43 gene, GDA gene, TMEM18 gene, and UGT2B10 gene), among the 8 genes;

$$\text{Best tumor response(ratio to tumor diameter baseline)} = 0.37664 + 96.360 \times A - 8.5128 \times B + 42.420 \times C + 26.810 \times D + 747.00 \times E \quad (1)$$

(wherein A represents an expression level of ALAD gene; B represents an expression level of C20orf43 gene; C represents an expression level of GDA gene; D represents an expression level of TMEM18 gene; and E represents an expression level of UGT2B10 gene) was established.

The formula (1) was indicated to have high predictability (R=0.8695, AICPS (Akaike's information criterion per sample)=−3.367294).

In order to verify the predictability of the formula (1), the expression levels of the 5 genes forming the formula (1) of the verification group (18 cases) were analyzed through Pearson's product-moment correlation analysis. As a result, the formula (1) was found to have high predictability (R=0.5840392 (p=0.01093)) (FIG. 1).

In the studies of the prediction formula, all combinations of 2 to 8 genes were investigated. Among the combinations, the combination of 5 genes; ALAD gene, C20orf43 gene, GDA gene, TMEM18 gene, and UGT2B10 gene, was found to provide a prediction formula with remarkably high precision. Surprisingly, ALAD gene and C20orf43 gene, each of which was found to have low correlation with the sensitivity, were selected among the 5 genes, while HOXB6 gene, which was found to have high correlation with the sensitivity, was not selected among the 5 genes.

The invention claimed is:

1. A method for determining the therapeutic response of a subject having colorectal cancer to which a FOLFOX6 regimen is administered the method comprising
administering anti-cancer agents according to said FOLFOX6 regimen to said subject;
obtaining a sample from said subject;
measuring the expression level of ALAD gene, C20orf43 gene, GDA gene, TMEM18 gene, and UGT2B10 gene in said sample to determine the best tumor response (ratio)
wherein the best tumor response (ratio) is calculated by measuring the expression level of ALAD gene, C20orf43 gene, GDA gene, TMEM18 gene, and UGT2B10 gene and then applying the formula:

Best tumor response(ratio)=$0.37664+96.360 \times A - 8.5128 \times B + 42.420 \times C + 26.810 \times D + 747.00 \times E \ldots$, wherein A represents an expression level of ALAD gene;
B represents an expression level of C20orf43 gene;
C represents an expression level of GDA gene;
D represents an expression level of TMEM18 gene; and
E represents an expression level of UGT2B10 gene;
correlating the best tumor response (ratio) to sensitivity to said FOLFOX6 regimen wherein when the obtained value is equal to or higher than a predetermined reference value, the cancer has sensitivity to the FOLFOX6 regimen, whereas when the obtained value is lower than the reference value, the cancer has no sensitivity to the FOLFOX6 regimen; and
either continuing administration of the FOLFOX6 regimen if sensitivity is determined to be present or discontinuing administration of the FOLFOX6 regimen if sensitivity is determined to be absent.

2. The method according to claim 1, wherein the reference value of the best tumor response (ratio) is 0.5 or higher.

3. The method according to claim 1, wherein the reference value of the best tumor response (ratio) is 0.7 or higher.

4. The method according to claim 1, wherein the expression level of the at least one gene is measured by an amount of mRNA expression of the at least one gene.

5. A method for determining the therapeutic response of a subject having colorectal cancer to which a FOLFOX6 regimen may be administered the method comprising
obtaining a sample from said subject before administration of the anti-cancer agents according to said FOLFOX6 regimen to said subject;
measuring the expression level of ALAD gene, C20orf43 gene, GDA gene, TMEM 18 gene, and UGT2B10 gene in said sample to determine the best tumor response (ratio)
wherein the best tumor response (ratio) is calculated by measuring the expression level of ALAD gene, C20orf43 gene, GDA gene, TMEM18 gene, and UGT2B10 gene and then applying the formula:
calculating best tumor response (ratio) by formula:

Best tumor response(ratio)=$0.37664+96.360 \times A - 8.5128 \times B + 42.420 \times C + 26.810 \times D + 747.00 \times E \ldots$, wherein A represents an expression level of ALAD gene;
B represents an expression level of C20orf43 gene;
C represents an expression level of GDA gene;
D represents an expression level of TMEM18 gene; and
E represents an expression level of UGT2B10 gene.
correlating the best tumor response (ratio) to sensitivity to said FOLFOX6 regimen wherein when the obtained value is equal to or higher than a predetermined reference value, the cancer has sensitivity to the FOLFOX6 regimen, whereas when the obtained value is lower than the reference value, the cancer has no sensitivity to the FOLFOX6 regimen; and
either administering the FOLFOX6 regimen if sensitivity is determined to be present or halting administering of the FOLFOX6 regimen if sensitivity is determined to be absent.

6. The method according to claim 5, wherein the reference value of the best tumor response (ratio) is 0.5 or higher.

7. The method according to claim 5, wherein the reference value of the best tumor response (ratio) is 0.7 or higher.

8. The method according to claim 5, wherein the expression level of the at least one gene is measured by an amount of mRNA expression of the at least one gene.

* * * * *

SEQUENCE LISTING

<160> NUMBER OF SEQ ID NOS: 1

<210> SEQ ID NO 1
<211> LENGTH: 25
<212> TYPE: DNA
<213> ORGANISM: Artificial sequence
<220> FEATURE:
<223> OTHER INFORMATION: Designed probe based on ALAD gene

<400> SEQUENCE: 1
gaggagtccc cagctattga ggcaa                          25